United States Patent [19]

Stoltefuss et al.

[11] 4,278,683

[45] Jul. 14, 1981

[54] SACCHARASE INHIBITING 3,4,5-TRIHYDROXYPIPERIDINE DERIVATIVES

[75] Inventors: Jürgen Stoltefuss, Haan; Lutz Müller, Wuppertal; Walter Puls, Wuppertal; Rüdiger Sitt, Wuppertal, all of Fed. Rep. of Germany

[73] Assignee: Bayer Aktiengesellschaft, Leverkusen, Fed. Rep. of Germany

[21] Appl. No.: 71,347

[22] Filed: Aug. 30, 1979

[30] Foreign Application Priority Data

Sep. 9, 1978 [DE] Fed. Rep. of Germany ....... 2839309

[51] Int. Cl.$^3$ ................. A61K 31/445; C07D 211/46; C07D 211/98
[52] U.S. Cl. ................................... 424/267; 424/249; 424/250; 424/251; 424/253; 424/258; 536/4; 536/18; 544/212; 544/238; 544/277; 546/24; 546/143; 546/159; 546/188; 546/193; 546/194; 546/207; 546/208; 546/210; 546/211; 546/214; 546/219; 546/220; 546/242
[58] Field of Search ...................... 546/242, 219, 220; 424/267

[56] References Cited

U.S. PATENT DOCUMENTS 4,182,767 1/1980 Murai et al. .......................... 424/267

OTHER PUBLICATIONS

Paulsen, H., et al., *Chem. Ber.*, 100, 802–815 (1967).
March, J., *Advanced Organic Chemistry*, McGraw Hill, New York, 1968, pp. 311, 660, 683 and 892.
Stamler, J., *Circulation*, 58(1), 3–19 (1978).
Lloyd, J., et al., *Postgrad. Med. J.* 54, 190–195 (1978).

*Primary Examiner*—Richard A. Schwartz
*Attorney, Agent, or Firm*—Sprung, Felfe, Horn, Lynch & Kramer

[57] ABSTRACT

The invention relates to 3,4,5-trihydroxypiperidines, processes for their producion, compositions containing them and methods for the use of said 3,4,5-trihydroxypiperidines and compositions containing them. The compounds and compositions of the invention are useful, inter alia, for their saccharase inhibiting activity in warm-blooded animals as well as their ability to improve feed utilization in warm-blooded and cold-blooded animals.

27 Claims, No Drawings

SACCHARASE INHIBITING 3,4,5-TRIHYDROXYPIPERIDINE DERIVATIVES

The present invention relates to new derivatives of 3,4,5-trihydroxypiperidine, to processes for their production and to their use against arteriosclerosis, diabetes, hyperlipaemia and adiposity, as well as their use in the nutrition of animals to influence the lean meat/fat ratio in favour of the proportion of lean meat.

According to the present invention we provide compounds which are 3,4,5-trihydroxypiperidine derivatives of the general formula

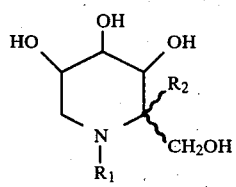

or a salt thereof in which $R_1$ denotes a hydrogen atom, an amino group, an optionally substituted straight-chain, branched or cyclic saturated or unsaturated aliphatic hydrocarbon radical or an optionally substituted aromatic of heterocyclic radical and $R_2$ denotes a —$CH_2NR_3R_4$, —$CH_2$—$NR_3$—CO—$R_4$, —$CH_2$—$NR_3$—$CONR_4R_5$, —$CH_2NR_3$—$SO_2R_4$, —$CH_2$—$NR_3$—$SO_2$—$NR_4R_5$, —$CH_2$—$NR_3$—CS—$R_4$, —$CH_2$—$NR_3$—CS—$NR_4R_5$, —COOH, —$CONH_2$, —$COOR_3$, —CO—$NR_3R_4$, —$CH_2$—$OR_3$, —$CH_2$—$NR_3$—$COOR_4$ or —$CH_2$—$NR_3$—$COSR_4$ group in which $R_3$, $R_4$ and $R_5$ independently denote a hydrogen atom, an optionally substituted, straight-chain, branched or cyclic saturated or unsaturated aliphatic hydrocarbon radical or an optionally substituted aromatic or heterocyclic radical.

Preferably, $R_1$, $R_3$, $R_4$ and $R_5$ independently of one another denote a hydrogen atom, an alkyl radical with 1 to 30, in particular 1 to 18, and especially 1 to 12, more especially 1 to 7 carbon atoms, an alkenyl radical or alkinyl radical with 2 to 18, preferably 3 to 10 carbon atoms, a monocyclic, bicyclic or tricyclic carbocyclic aliphatic radical with 3 to 10 carbon atoms, which can be saturated, monounsaturated or diunsaturated, a monocyclic or bicyclic carbocyclic aryl radical with 6 or 10 carbon atoms or a heterocyclic radical which has 3 to 8, preferably 3 to 6, ring members and optionally contains 1, 2, 3 or 4 hetero-atoms, in particular N, O and S, and onto which a benzene ring or a further heterocyclic ring of the type mentioned can be fused, it being possible for the radicals mentioned to carry 1 to 5, preferably 1, 2 or 3, substituents.

Examples which may be mentioned of possible substituents for alkyl are: hydroxyl, or alkoxy with preferably 1 to 4 carbon atoms, in particular methoxy and ethoxy; acyloxy, the acyl radical being derived from aliphatic (particularly alkane) carboxylic acids with 1 to 7 carbon atoms, aromatic carboxylic acids, preferably phenylcarboxylic acids, which can be substituted in the phenyl radical by hydroxyl, halogen, preferably fluorine, chlorine or bromine, pseudohalogen, preferably trifluoromethyl, $C_1$ to $C_4$ alkyl, $C_1$ to $C_4$ alkoxy, nitro and/or amino, or heterocyclic carboxylic acids which are derived from 5-membered or 6-membered heterocyclic compounds which contain 1 to 3 hetero-atoms (N, O and S) and can be substituted in the heterocyclic ring by $C_1$ to $C_4$ alkyl, chlorine, bromine or amino; trifluoromethyl; amino, monoalkylamino and dialkylamino with preferably 1 to 4 carbon atoms per alkyl radical, preferably monomethylamino, monoethylamino, dimethylamino and diethylamino, and monoacylamino, the acyl radical being derived from aliphatic (preferably alkane) carboxylic acids with 1 to 7 carbon atoms, aromatic carboxylic acids, preferably phenylcarboxylic acids, which can be substituted in the phenyl radical by hydroxyl, halogen, in particular F, Cl or Br, $C_1$ to $C_4$ alkyl, $C_1$ to $C_4$ alkoxy, nitro and/or amino, or heterocyclic carboxylic acids which are derived from 5-membered or 6-membered heterocyclic compounds which contain 1 to 3 hetero-atoms (N, O and S) and can be substituted in the heterocyclic ring by $C_1$ to $C_4$ alkyl, chlorine, bromine or amino; mercapto, and alkylthio with preferably 1 to 4 carbon atoms, preferably methylthio and ethylthio; halogen, preferably fluorine, chlorine and bromine; pseudohalogen, preferably trifluoromethyl, alkylcarbonyl with preferably 1 to 4 carbon atoms in the alkyl radical; carboxyl, nitro, cyano, the aldehyde group and the sulphonic acid group; and heterocyclic radicals of the above-mentioned type, preferably also heterocyclic radicals derived from sugars, very particularly from hexoses or pentoses, which can be bonded to the alkyl radical directly via a ring atom or via a —O—, —S— or —NH— bridge.

Examples of heterocyclic substituents of the alkyl radicals are: phthalimido, pyridyl, thienyl, furyl, isoxazolyl, thiazolyl, glucopyranosyl, ribofuranoxyl, oxiranyl and the like.

Furthermore, suitable substituents of the alkyl radicals are aromatic radicals, such as naphthyl and, in particular, phenyl, which can carry one or more, preferably 1 to 3, identical or different substituents selected from —OH, —$NH_2$, $C_1$ to $C_4$ alkyl—NH—, ($C_1$ to $C_4$ alkyl)$_2$—N—, $C_1$ to $C_4$ alkoxy, $NO_2$, —CN, —COOH, —COO—$C_1$ to $C_4$ alkyl, $C_1$ to $C_6$ alkyl, halogen, preferably fluorine, chlorine or bromine, trifluoromethyl, preferably trifluoromethyl; $C_1$ to $C_4$ alkylthio, —SH, $C_1$ to $C_4$ alkylsulphonyl, —$SO_3H$, —$SO_2NH_2$ and —$SO_2$—NH—$C_1$ to $C_4$ alkyl.

The alkyl radical can also carry a monocyclic, bicylic or tricyclic substituent with preferably 3 to 10 carbon atoms, which can in turn be substituted by hydroxyl, amino, halogen, in particular fluorine, chlorine or bromine, pseudohalogen, in particular trifluoromethyl, or —COOH.

The alkyl radical preferably carries substituents such as hydroxyl, alkoxy with 1 to 4 carbon atoms, mercapto, alkylthio with 1 to 4 carbon atoms, halogen, pseudohalogen, nitro, amino, monoalkylamino with 1 to 4 carbon atoms and acylamino, the acyl radical being derived from aliphatic carboxylic acids with 1 to 6 carbon atoms.

Possible substituents for the monocyclic, bicyclic or tricyclic aliphatic radicals, $R_1$, $R_3$, $R_4$ and $R_5$, are those mentioned for alkyl radicals.

The aryl radicals can carry one or more, preferably 1 to 3, identical or different substituents.

Examples of substituents which may be mentioned are: alkyl with 1 to 10 carbon atoms, which in turn can be substituted again, for example by chlorine, nitro or cyano; optionally substituted alkenyl radicals with 2 to 10 carbon atoms; hydroxyl, and alkoxy with preferably 1 to 4 carbon atoms; amino, and monoalkylamino and dialkylamino with preferably 1 to 4 carbon atoms per alkyl radical; mercapto, and alkylthio with preferably 1 to 4 carbon atoms; carboxyl, carbalkoxy with preferably 1 to 4 carbon atoms, the sulphonic acid group, alkylsulphonyl with preferably 1 to 4 carbon atoms and arylsulphonyl, preferably phenylsulphonyl; aminosulphonyl, and alkylamino- and dialkylamino-sulphonyl with 1 to 4 carbon atoms per alkyl group, preferably methyl- and dimethyl-aminosulphonyl; nitro, cyano or the aldehyde group; alkylcarbonylamino with preferably 1 to 4 carbon atoms; and alkylcarbonyl with 1 to 4 carbon atoms, benzoyl, benzylcarbonyl and phenylethylcarbonyl, it being possible for the last alkyl, phenyl, benzyl and phenylethyl radicals mentioned to be in turn substituted again, for example by chlorine, nitro or hydroxyl.

The heterocyclic radicals are preferably derived from hetero-paraffinic, hetero-aromatic or hetero-olefinic 5-membered or 6-membered rings with preferably 1 to 3 identical or different hetero-atoms. Possible hetero-atoms are oxygen, sulphur or nitrogen. These ring systems can carry further substituents, such as, for example, hydroxyl, amino or $C_1$ to $C_4$ alkyl groups, or benzene nuclei or further, preferably 6-membered, heterocyclic rings of the type mentioned can be fused onto them.

Particularly preferred heterocyclic radicals are derived, for example, from furane, pyrane, pyrrolidine, piperidine, pyrazole, imidazole, pyrimidine, pyridazine, pyrazine, triazine, pyrrole, pyridine, benzimidazole, quinoline, isoquinoline or purine.

Preferred compounds correspond to the general formula

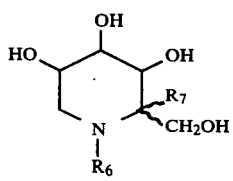

or a salt thereof, in which $R_6$ denotes a hydrogen atom or a $C_1$ to $C_{12}$ alkyl or phenyl-$C_1$ to $C_4$ alkyl group $R_7$ denotes —CH$_2$—NHR$_8$, —CH$_2$—NHCOR$_9$, —CH$_2$—NH—SO$_2$NR$_8$R$_9$, —CH$_2$—NH—CONHR$_8$, —CH$_2$—NH—SO$_2$R$_9$, —CH$_2$—NH—CSNHR$_8$, —CONH$_2$, —CONR$_8$R$_9$, —COOR$_8$ or —CH$_2$OH, $R_8$ denotes a hydrogen atom or independently of $R_9$, has any of those meanings given for $R_9$, and $R_9$ denotes a $C_1$ to $C_{10}$ alkyl, allyl or $C_5$ or $C_6$ cycloalkyl group, a phenyl radical which is optionally substituted by methyl, methoxy, chlorine or nitro, a benzyl radical which is optionally substituted by methyl, methoxy, chlorine or a nitro, pyridylmethyl or furylmethyl group.

It has been found that the new compounds of the present invention are potent inhibitors for α-glucosidases, in particular for disaccharidases. The new compounds of the present invention are thus valuable agents for influencing a number of metabolic processes and thus enrich the range of medicaments. Compared with 2-hydroxymethyl-3,4,5-trihydroxypiperidine, known from DT-OS (German Published Specification) No. 2,656,602, the new compounds have advantageous therapeutic properties.

According to the present invention there is further provided a process for the production of a compound of the present invention in which (a) a compound of the formula

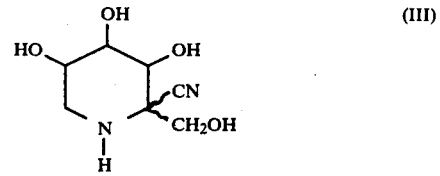

is catalytically hydrogenated to give the compound of the formula

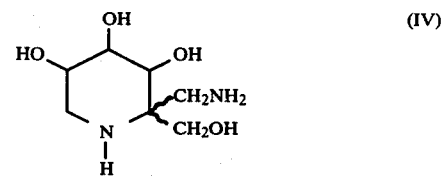

and the primary amino group is then optionally alkylated, acylated, sulphonylated or reacted with an isocyanate or isothiocyanate, and the secondary nitrogen atom is then optionally alkylated, or (b) a compound of the formula III as defined above is saponified to give the compound of the formula

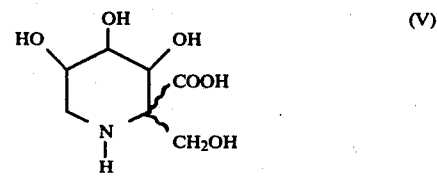

which is then optionally esterified and the ester is either optionally reacted with an amine to give an amide or optionally reduced with a hydrogen donor reducing agent to give a compound of the formula

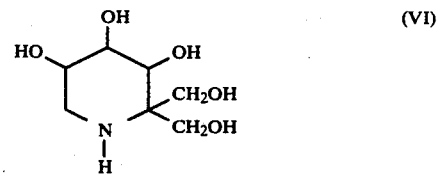

and the compound formed in this way is optionally alkylated on the secondary nitrogen atom, or (c) a compound of the general formula

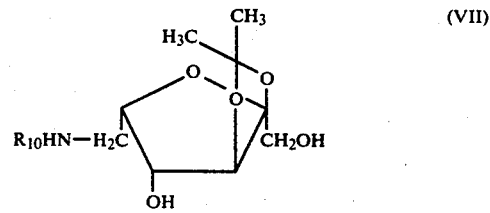

in which $R_{10}$ denotes an optionally substituted straight-chain, branched or cyclic, saturated or unsaturated aliphatic hydrocarbon radical or an optionally substituted aromatic or heterocyclic radical, is deblocked with a mineral acid to give a compound of the general formula

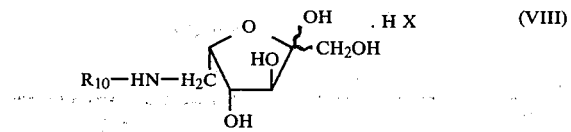
(VIII)

in which $R_{10}$ has the meaning given above, which is then reacted directly in solution, or after isolation, with a cyanide to give a compound of the general formula

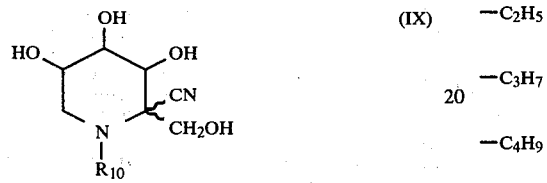
(IX)

in which $R_{10}$ has the meaning given above and is catalytically hydrogenated and the resulting primary amino group is then optionally alkylated, acylated, sulphonylated or reacted with an isocyanate or isothiocyanate.

Most of the starting compounds used are known, or they can easily be prepared by methods which are in themselves known (compare H. Paulsen, J. Sangster and K. Heyns, Chem. Ber. 100, 802–815 (1967)).

Examples of hydrogen donor reducing agents which can be used are catalytic hydrogen, alkali metal borohydrides, alkali metal cyanoborohydrides, dialkylaminoboranes or formic acid. Sodium cyanoborohydride is preferably used in the reductive amination to give N-alkylamines and hydrogen in the presence of Raney nickel or in the presence of nobel metal catalysts is preferably used in the hydrogenation of the nitrile group to give the aminomethyl group. Preferably the hydrogenation is carried out under hydrogen pressures of 1 to 150 bars and at temperatures between 20° and 150° C., preferred solvents being protic, polar solvents, in particular water and alcohols.

Most of the aldehydes, ketones, carboxylic acid chlorides, sulphonic acid chlorides, sulphamoyl chlorides, isocyanates and isothiocyanates employed in the process are known. New compounds of these groups can be prepared according to conventional methods. Examples which may be mentioned are formaldehyde, acetaldehyde, propionaldehyde, butyraldehyde, 1-pentanal, 1-hexanal, acetone, 4-heptanone, cyclohexanone, cyclopentanone, benzaldehyde, 4-pyridinealdehyde, furfural, acetyl chloride, propionyl chloride, butyric acid chloride, benzoyl chloride, 4-methoxybenzoyl chloride, 3-methylbenzoyl chloride, methanesulphonic acid chloride, benzenesulphonic acid chloride, dimethylcarbamoyl chloride, ethyl isocyanate, phenyl isocyanate, 4-chlorophenyl isocyanate, methyl isocyanate, 4-toluenesulphonic acid chloride, dimethylsulphamoyl chloride, methyl isothiocyanate, butyl isocyanate, hexyl isocyanate, allyl isothiocyanate and phenyl isothiocyanate.

New active compounds which may be mentioned specifically are

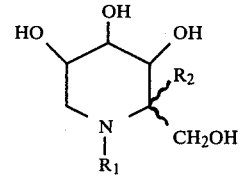

| $R_1$ | $R_2$ |
|---|---|
| H | $-CH_2-NH_2$ |
| H | $-CH_2-NH-CO-C_6H_5$ |
| $-CH_3$ | $-CH_2-NH-CO-C_6H_5$ |
| $-C_2H_5$ | $-CH_2-NH-CO-C_6H_5$ |
| $-C_3H_7$ | $-CH_2-NH-CO-C_6H_5$ |
| $-C_4H_9$ | $-CH_2-NH-CO-C_6H_5$ |
| $-C_5H_{11}$ | $-CH_2-NH-CO-C_6H_5$ |
| $-C_6H_{13}$ | $-CH_2-NH-CO-C_6H_5$ |
| $-C_7H_{15}$ | $-CH_2-NH-CO-C_6H_5$ |
| $-C_8H_{17}$ | $-CH_2-NH-CO-C_6H_5$ |
| $-C_{10}H_{21}$ | $-CH_2-NH-CO-C_6H_5$ |
| $-C_{12}H_{25}$ | $-CH_2-NH-CO-C_6H_5$ |
| $-C_{14}H_{29}$ | $-CH_2-NH-CO-C_6H_5$ |
| H | $-CH_2-NH-CO-C_6H_4-NO_2$ |
| $-C_9H_{19}$ | $-CH_2-NH-CO-C_6H_4-NO_2$ |
| H | $-CH_2-NH-CO-C_6H_4-CH_3$ |
| $-CH_3$ | $-CH_2-NH-CO-C_6H_4-CH_3$ |
| $-C_8H_{17}$ | $-CH_2-NH-CO-C_6H_4-CH_3$ |
| $-H$ | $-CH_2-NH-CO-C_6H_4-OCH_3$ |
| $-C_2H_5$ | $-CH_2-NH-CO-C_6H_4-OCH_3$ |
| $-H$ | $-CH_2-NH-SO_2-C_6H_4-CH_3$ |
| $-CH_3$ | $-CH_2-NH-SO_2-C_6H_4-CH_3$ |
| $-C_2H_5$ | $-CH_2-NH-SO_2-C_6H_4-CH_3$ |
| $-C_4H_9$ | $-CH_2-NH-SO_2-C_6H_4-CH_3$ |

Table (Column 7, continued)

Structure:

$$\text{HO-}\underset{R_1}{\underset{|}{N}}\text{-piperidine with OH, OH, }R_2\text{, CH}_2\text{OH substituents}$$

| $R_1$ | $R_2$ |
|---|---|
| $-C_7H_{15}$ | $-CH_2-NH-SO_2-C_6H_4-CH_3$ |
| $-C_9H_{19}$ | $-CH_2-NH-SO_2-C_6H_4-CH_3$ |
| $-C_{11}H_{23}$ | $-CH_2-NH-SO_2-C_6H_4-CH_3$ |
| H | $-CH_2-NH-SO_2-C_6H_5$ |
| $-CH_3$ | $-CH_2-NH-SO_2-C_6H_5$ |
| $C_8H_{17}$ | $-CH_2-NH-SO_2-C_6H_5$ |
| H | $-CH_2-NH-SO_2-C_6H_4-Cl$ |
| $CH_3$ | $-CH_2-NH-SO_2-C_6H_4-Cl$ |
| H | $-CH_2-NH-CO-NH-CH_3$ |
| $-CH_3$ | $-CH_2-NH-CO-NH-CH_3$ |
| $-C_6H_{13}$ | $-CH_2-NH-CO-NH-CH_3$ |
| $-CH_2-CH=CH_2$ | $-CH_2-NH-CO-C_6H_5$ |
| $-CH_2-CH=CH_2$ | $-CH_2-NH-SO_2-C_6H_4-CH_3$ |
| $-CH_2-CH=CH_2$ | $-CH_2-NH-CO-NH-CH_3$ |
| $-H$ | $-CH_2-NH-CO-NH-C_6H_5$ |
| $-CH_3$ | $-CH_2-NH-CO-NH-C_6H_5$ |
| $-C_7H_{15}$ | $-CH_2-NH-CO-NH-C_6H_5$ |
| H | $-CH_2-NH-CO-CH_3$ |
| $-CH_3$ | $-CH_2-NH-CO-CH_3$ |
| $-C_2H_5$ | $-CH_2-NH-CO-CH_3$ |
| $-C_8H_{17}$ | $-CH_2-NH-CO-CH_3$ |
| H | $-CH_2-NH-CO-C_2H_5$ |
| $-CH_3$ | $-CH_2-NH-CO-C_2H_5$ |
| H | $-CH_2-NH-CO-C_3H_7$ |
| $-C_2H_5$ | $-CH_2-NH-CO-C_3H_7$ |
| H | $-CH_2-NH-CO-C_6H_{13}$ |
| $-CH_3$ | $-CH_2-NH-CO-C_6H_{13}$ |
| H | $-CH_2-NH-CO-C_8H_{17}$ |
| $-C_6H_{13}$ | $-CH_2-NH-CO-C_8H_{17}$ |
| H | $-CH_2-NH-CO-C_{17}H_{35}$ |
| $-CH-C\equiv CH$ | $-CH_2-NH-CO-C_{17}H_{35}$ |
| H | $-CH_2-N(CH_3)-CO-C_6H_5$ |
| $-CH_3$ | $-CH_2-N(CH_3)-CO-C_6H_5$ |
| H | $-CH_2-NH-CS-NH-CH_3$ |
| $CH_3$ | $-CH_2-NH-CS-NH-CH_3$ |
| H | $-CH_2-NH-CS-NH-C_6H_5$ |

Table (Column 8, continued)

| $R_1$ | $R_2$ |
|---|---|
| $-C_4H_9$ | $-CH_2-NH-CS-NH-C_6H_5$ |
| H | $-CH_2-NH-COOC_2H_5$ |
| $CH_3$ | $-CH_2-NH-COOC_2H_5$ |
| H | $-CH_2-NH-CO-SC_2H_5$ |
| $CH_3$ | $-CH_2-NH-COSC_2H_5$ |
| H | $-CH_2-NH-SO_2-CH_3$ |
| $CH_3$ | $-CH_2-NH-SO_2-CH_3$ |
| H | $-CH_2-NH-SO_2-N(CH_3)_2$ |
| $C_2H_5$ | $-CH_2-NH-SO_2-N(CH_3)_2$ |
| H | $-CH_2-NH-C_4H_9$ |
| $CH_3$ | $-CH_2-NH-C_8H_{17}$ |
| $CH_3$ | $-CH_2-N(CH_3)_2$ |
| $C_6H_5-CH_2-$ | $-CH_2-NH-CO-C_6H_5$ |
| $C_6H_5-CH_2-$ | $-CH_2-NH-SO_2-C_6H_5$ |
| $C_6H_5-CH_2-$ | $-CH_2-NH-CO-NH-CH_3$ |
| $C_6H_5-CH_2-$ | $-CH_2-NH-CO-NH-C_6H_5$ |
| $C_6H_5-CH_2-CH_2-$ | $-CH_2-NH-CO-NH-C_6H_5$ |
| $C_6H_5-CH_2-CH_2-$ | $-CH_2-NH-CO-C_6H_5$ |
| H | $-COOH$ |
| H | $-COOC_2H_5$ |
| $CH_3$ | $-COOH$ |
| $C_8H_{17}$ | $-COOH$ |
| $CH_3$ | $-COOC_2H_5$ |
| H | $-CONH_2$ |
| $CH_3$ | $-CONH_2$ |
| $CH_3$ | $-CH_2-NH-SO_2C_3H_7$ |
| H | $-CH_2OH$ |
| $CH_3$ | $-CH_2OH$ |
| H | $-CH_2-O-COCH_3$ |
| $CH_3$ | $-CH_2-O-COCH_3$ |
| H | $-COOC_8H_{17}$ |
| $-CH_3$ | $-COOC_8H_{17}$ |
| $-C_6H_{13}$ | $-COOC_8H_{17}$ |
| $HO-CH_2-CH_2-$ | $-CH_2-NH-CO-C_6H_5$ |
| $-CH_2-C\equiv CH$ | $-CH_2-NH-CO-C_6H_5$ |
| $-CH_3$ | $-CH_2-NH-CH_2-CH_2-CN$ |

The inhibitors according to the invention are suitable as therapeutic agents for the following indications: arteriosclerosis, adiposity, diabetes and hyperlipaemia.

To broaden the action spectrum, it can be advisable to combine inhibitors for glycoside hydrolases which complement one another in their action, the combinations being either combinations of the inhibitors according to the invention with one another or combinations of the inhibitors according to the invention with inhibitors which are already known. Thus, for example, it can be appropriate to combine saccharase inhibitors according to the invention with amylase inhibitors which are already known.

In some cases, combinations of the inhibitors according to the invention with known oral antidiabetic agents ($\beta$-cytotropic sulphonylurea derivatives and/or biguanides having an action on the blood sugar) and with active compounds which lower the blood lipid level, such as, for example, clofibrate, nicotinic acid, cholestyramine and others, are also advantageous.

As stated above, the invention also relates to the use in medicine of the compounds of the invention.

The present invention provides a pharmaceutical composition containing as active ingredient a compound of the invention in admixture with a solid, liquid or liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth)) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solution and emulsions of the active ingredient in aqueous or non-aqueous diluents or syrups.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and soritane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 mg to 5 g of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally. Preferred pharmaceutical compositions and medicaments are therefore those adapted for administration such as oral administration. Administration in the method of the invention is preferably oral administration.

In general it has proved advantageous to administer amounts of from 0.1 mg to 100 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

In addition to the use of compounds of the invention in pharmaceutical compositions, foodstuffs containing these active compounds can also be prepared, for example sugar, bread, potato products, fruit juice, beer, chocolate and other confectionery, and preserves, such as, for example, jam, and in this case a therapeutically effective amount of at least one of the inhibitors according to the invention is added to these products.

The foodstuffs produced using the active compounds according to the invention are suitable both for the diet of patients suffering from metabolism disorders and for the nutrition of healthy persons in the sense of a diet which prevents metabolism disorders.

The inhibitors according to the invention furthermore have the property of influencing to a great extent the relationship between the proportion of undesired fat to the proportion of desired meat of low fat content (lean meat) in animals in favour of the lean meat. This is of particular importance for rearing and keeping agricultural livestock, for example in the fattening of pigs, but is also of considerable importance for rearing and keeping other livestock and pets. Using the inhibitors can furthermore lead to a considerable rationalisation of feeding of animals, from the point of view of time, quantity and quality. Since they cause a certain delay in digestion, the residence time of the nutrients in the digestive tract is extended and this makes possible ad libitum feeding, which is associated with a low expenditure. Moreover, using the inhibitors according to the invention in many cases results in a considerable saving of valuable protein feed.

The active compounds can thus be used in virtually all fields of animal nutrition as agents for reducing the deposition of fat and for saving feed protein.

The activity of the active compounds is largely independent of the species and sex of the animals. The active compounds prove particularly valuable in the case of species of animals which, generally or at certain periods of their life, tend to deposit relatively large amounts of fat.

The following livestock and pets may be mentioned as examples of animals for which the inhibitors can be employed for reducing the deposition of fat and/or for saving feed protein: warm-blooded animals, such as cattle, pigs, horses, sheep, goats, cats, dogs, rabbits, fur-bearing animals, for example mink and chinchillas, other pets, for example guinea pigs and hamsters, laboratory animals and zoo animals, for example rats, mice, apes and the like, and poultry, for example broilers, hens, geese, ducks, turkeys, pigeons, parrots and canaries, and cold-blooded animals, such as fish, for example carp, and reptiles, for example snakes.

Because of the favourable properties of the active compounds, the amount of the active compounds which is administered to the animals to achieve the desired effect can be varied substantially. It is preferably about 0.1 mg to 1.0 g and in particular 1 to 100 mg/kg of feed per day. The period of administration can be from a few hours or days up to several years. The appropriate amount of active compound and the appropriate period of administration are closely related to the aim of feeding. They depend, in particular, on the species, age, sex, state of health and nature of keeping of the animals and can easily be determined by any expert.

The active compounds according to the invention are administered to the animals by the customary methods. The nature of the administration depends, in paticular, on the species, the behaviour and the general condition of the animals. Thus, administration can be effected orally once or several times daily at regular or irregular intervals. For reasons of expediency, in most cases oral administration, in particular in the rhythm of the intake of food and/or drink by the animals, is to be preferred.

The active compounds can be administered as pure substances or in the formulated form, the formulated form being understood as a premix, that is to say as a mixture with non-toxic inert carriers of any desired nature, as a part of a total ration in the form of a supplementary feed or as a mixing component of a mixed feed for use by itself. Administration of suitable formulations via the drinking water is also included.

The active compounds, optionally in the formulated form, can also be administered in a suitable form together with other nutrients and active compounds, for example mineral salts, trace elements, vitamins, proteins, energy carriers (for example starch, sugars, fats), dyestuffs and/or flavouring agents or other feed additives, such as, for example, growth promoters. The active compounds can be administered to the animals before, during or after intake of the feed.

Oral administration together with the feed and/or drinking water is recommended, the active compounds being added to all or parts of the feed and/or drinking water as required.

Accordingly the present invention also provides a medicated fodder comprising an active compound of the present invention and a nutritious material.

The active compounds can be admixed to the feed and/or drinking water in accordance with customary methods by simple mixing as pure substances, preferably in the finely divided form or in the formulated form mixed with edible, non-toxic carriers, and optionally also in the form of a premix or a feed concentrate.

The feed and/or drinking water can contain the active compounds according to the invention in a concentration of, for example, about 0.001 to 5.0%, in particular 0.02 to 2.0% (by weight). The optimum level of the concentration of the active compound in the feed and/or drinking water depends, in particular, on the amount of feed and/or drinking water taken in by the animals and can easily be determined by any expert.

The nature of the feed and its composition is irrelevant in this context. All the customary, commercially available or specific feed compositions, which preferably contain the customary equilibrium of energy substances and proteins, including vitamins and mineral substances, necessary for balanced nutrition, can be used. The feed can be composed, for example, of vegetable substances, for example shredded oilcake, shredded cereal and cereal by-products, and also hay, silage fodder, beet and other forage plants, of animal substances, for example meat products and fish products, bone meal, fats, vitamins, for example A, D, E, K and B complex, and specific sources of protein, for example yeasts, and certain aminoacids and mineral substances and trace elements, such as, for example, phosphorus and iron, zinc, manganese, copper, cobalt, iodine and the like.

Premixes can preferably contain about 0.1 to 50%, in particular 0.5 to 5.0% (by weight) of an active compound according to the invention, in addition to any desired edible carriers and/or mineral salts, for example carbonated feed lime, and are prepared by the customary mixing methods.

Mixed feeds preferably contain 0.001 to 5.0%, in particular 0.02 to 2.0% (by weight) of an active compound according to the invention, in addition to the customary raw material components of a mixed feed, for example shredded cereal or cereal by-products, shredded oilcake, animal protein, minerals, trace elements and vitamins. They can be prepared by the customary mixing methods.

In premixes and mixed feedstuffs, preferably, the active compounds can also optionally be protected from air, light and/or moisture by suitable agents which coat their surface, for example with non-toxic waxes or gelatine.

The following is an example of the composition of a finished mixed feed for poultry, which contains an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodinated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin D$_3$, 10 mg of vitamin E, 1 mg of vitamin K$_3$, 3 mg of riboflavin, 2 mg of pyridoxine, 20 mg of vitamin B$_{12}$, 5 mg of calcium pantothenate, 30 mg of nicotinic acid, 200 mg of choline chloride, 200 g of MnSO$_4 \times$H$_2$O, 140 mg of ZnSO$_4 \times$7H$_2$O, 100 mg of FeSO$_4 \times$7H$_2$O and 20 mg of CuSO$_4 \times$5H$_2$O.

The active compound premix contains as active compound according to the invention in the desired amount, for example 1,600 mg, and in addition 1 g of DL-methionine as well as an amount of soya bean meal such that 3.2 g of premix are formed.

The following is an example of the composition of a mixed feed for pigs, which contains an active compound of the formula I: 630 g of shredded cereal feed (composed of 200 g of shredded maize, 150 g of shredded barley, 150 g of shredded oats and 130 g of shredded wheat), 80 g of fish meal, 60 g of coarse soya bean meal, 58.8 g of tapioca meal, 38 g of brewer's yeast, 50 g of a vitamin/mineral mixture for pigs (composition, for example, as for the chick feed), 30 g of linseed cake meal, 30 g of maize gluten feed, 10 g of soya bean oil, 10 g of sugarcane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

The inhibitors can be used individually or in any desired mixtures with one another.

IN VITRO SACCHARASE INHIBITION TEST

The in vitro saccharase inhibition test makes it possible to determine the inhibitory activity of a substance on the enzyme by comparing the activity of solubilised intestinal disaccharidase complex in the presence and in the absence (so-called 100% value) of the inhibitor. A virtually glucose-free sucrose (glucose <100 ppm) is used as the substrate which determines the specificity of the inhibition test; the determination of the enzyme activity is based on the spectrophotometric determination of liberated glucose by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit=SU); the saccharase unit is thereby defined as the enzyme activity which, under the given conditions, splits one $\mu$mol of sucrose per minute and thus leads to the liberation of one $\mu$mol each of glucose, which is determined in the test, and fructose, which is not recorded in the test.

The intestinal disaccharidase complex is obtained from swine small intestine mucosa by tryptic digestion, precipitation from 66% strength ethanol at $-20°$ C., taking up of the precipitate in 100 mM phosphate buffer of pH 7.0 and finally dialysis against the same buffer.

100 $\mu$l of a dilution of the intestinal disaccharidase complex in 0.1 M maleate buffer of pH 6.25 are added to 10 $\mu$l of a sample solution which is made up such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SU/ml.

The saccharolytic reaction is then started by adding 100 $\mu$l of a 0.4 M solution of sucrose ("SERVA 35579") in 0.1 M maleate buffer of pH 6.25 and, after an incubation period of 20 minutes at 37° C., is stopped by adding 1 ml of glucose dehydrogenase reagent (1 small bottle of a lyophilised glucose dehydrogenase/mutarotase mixture ("MERCK 14053") and 331.7 mg of $\beta$-nicotinamideadenine dinucleotide (free acid, "BOEHRINGER", degree of purity I) dissolved in 250 ml of 0.5 M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharase inhibitor of the formula $C_{25}H_{43}O_{18}N$ which has a specific inhibitory activity of 77,700 SIU/g and, when employed in the test in amounts of 10 to 20 ng, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between the 100% value and the batch inhibited by the sample solution, taking into consideration the amount of inhibitor employed.

The following Examples illustrate processes for the preparation of compounds according to the present invention, except Example 1, which illustrates the preparation of a starting material.

EXAMPLE 1

2,6-Imino-2-hydroxymethyl-2,6-didesoxy-L-ido(L-gulo)-hexonic acid nitrile 14.7 g of sodium cyanide are added to a solution of 46.6 g of 6-amino-6-desoxy-L-sorbofuranose hydrochloride monohydrate in 200 ml of 0.5 N hydrochloric acid and the mixture is stirred for 3 hours. It is then concentrated in vacuo at 25° C. until it is a thin syrup, 200 ml of methanol/ethanol (1:1) are added and the salt which has separated out is filtered off. The filtrate is concentrated in vacuo at 25° C. and the resulting crystalline solid is stirred with ethanol, filtered off and washed with ethanol and diethyl ether. 34.5 g (92% of theory) of colourless crystals of melting point 156° C. (decomposition) are obtained.

Rf value=0.194 (running agent 1)
Rf value=0.119 (running agent 2)
Rf value=0.6 (running agent 3)
Running agent 1=chloroform/methanol/25% strength ammonia in the volume ratio 6:4:1
Running agent 2=chloroform/ethyl acetate/methanol/25% strength ammonia solution in the volume ratio 40:40:30:1
Running agent 3=ethyl acetate/methanol/water/25% strength ammonia solution in the volume ratio 120:70:10:2.

EXAMPLE 2

2-Amino-methyl-2-hydroxymethyl-3,4,5-trihydroxypiperidine

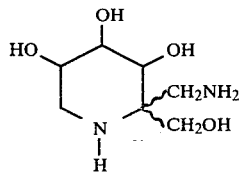

15 g of 2,6-imino-2-hydroxymethyl-2,6-didesoxy-L-ido(L-gulo)-hexonic acid nitrile are dissolved in 200 ml of water and, after adding Raney nickel, are catalytically hydrogenated under a pressure of 3.5 bars. The catalyst is filtered off and the solution is concentrated in vacuo at 25° C. The evaporation residue is stirred with 300 ml of methanol at 40° C. and, after adding a filtration auxiliary, the mixture is filtered. After concentrating the light yellow filtrate, 11.4 g (75% of theory) of the desired compound is obtained in the form of a yellowish foam. Rf value=0.34 (Merck TLC plates precoated with silica gel 60 F 254, running agent: methanol/chloroform/25% strength ammonia 90:60:60).

EXAMPLE 3

2-Benzoylaminomethyl-2-hydroxymethyl-3,4,5-trihydroxypiperidine

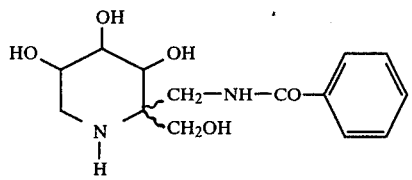

2.0 g of 2-aminomethyl-2-hydroxymethyl-3,4,5-trihydroxypiperidine are dissolved in 20 ml of methanol/water (1:1), 1.45 ml of triethylamine are added and the mixture is cooled to −10° C. After adding 1.635 g of benzoyl chloride, the mixture is stirred at −10° C. for 30 minutes and then at room temperature for 20 hours. The solution is evaporated in vacuo and the residue is taken up in 40 ml of methanol/water (2:1). This solution is discharged onto a column 40 cm long and 3 cm wide which is filled with a cation exchanger in the H+ form. The column is first washed with 1 l of a methanol/water mixture (2:1) and is then eluted with 0.1% strength ammonia in methanol/water (2:1). The individual fractions are examined by thin layer chromatography to determine their content of the required compound. The fractions containing the desired product are collected and evaporated. The residue is dissolved in a little methanol and the solution is left to stand, whereupon crystallisation soon starts. The mixture is diluted with a little isopropanol and the crystals are filtered off and washed with isopropanol and diethyl ether. 0.8 g of 2-benzoylamino-2-hydroxymethyl-3,4,5-trihydroxypiperidine of melting point 154° to 156° C. is obtained.

Rf value=0.374 (running agent 1).

EXAMPLE 4

2-(4-Nitrobenzoylaminomethyl)-2-hydroxymethyl-3,4,5-trihydroxypiperidine 5.4 g of 2-aminomethyl-2-hydroxymethyl-3,4,5-trihydroxypiperidine are dissolved in 50 ml of a methanol/water mixture (1:1), and 3.92 ml of triethylamine and, at −5° C., 5.44 g of 4-nitrobenzoyl chloride are added. The mixture is stirred for 24 hours and evaporated in vacuo, the residue is taken up in ether/water and the phases are separated. The aqueous phase is extracted once with ether and the product phase is then evaporated. The residue is dissolved in a little water and the solution is discharged onto a column 120 cm long and 4 cm wide which contains cellulose as the stationary phase and 99% pure acetone as the mobile phase. The column is eluted successively with 99% pure acetone, 95% pure acetone and finally 90% pure acetone. The individual fractions are examined by thin layer chromatography to determine their content of the required compound. The fractions containing the desired product are collected and evaporated. 2.6 g of 2-(4-nitrobenzoylaminomethyl)-2-hydroxymethyl-3,4,5-trihydroxypiperidine are obtained.

Rf value: 0.19 (TLC pre-coated plates, silica gel 60, running agent: chloroform/ethyl acetate/methanol/25% strength ammonia 80:80:80:2).

Rf value=0.383 (running agent 1).

EXAMPLE 5

2-(4-Methoxybenzoylaminomethyl)-2-hydroxymethyl-3,4,5-trihydroxypiperidine was prepared analogously to Example 4.

Rf value=0.407 (running agent 1)

EXAMPLE 6

2-(4-Chlorobenzoylaminomethyl)-2-hydroxymethyl-3,4,5-trihydroxypiperidine was prepared analogously to Example 4.

Rf value=0.402 (running agent 1)

EXAMPLE 7

2-(4-Toluenesulphamidomethyl)-2-hydroxymethyl-3,4,5-trihydroxypiperidine

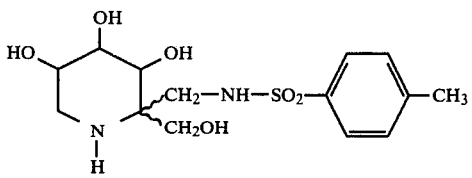

3.7 g of 2-aminomethyl-2-hydroxymethyl-3,4,5-trihydroxypiperidine were dissolved in 40 ml of methanol/water (1:1), and 4.2 g of 4-toluenesulphonyl chloride were added at 0° C. The mixture was stirred at 0° C. for 30 minutes, at 20° C. for 1 hour and at 50° C. for 30 minutes. It was diluted with 30 ml of water and extracted twice with diethyl ether. 3 ml of 25% strength ammonia were added to the aqueous phase, the mixture was evaporated, the residue was dissolved in a little water and the solution was discharged onto a column 100 cm long and 3 cm wide which contains cellulose as the stationary phase and n-butanol as the mobile phase. The column was eluted successively with n-butanol, 97.5% pure n-butanol and 95% pure n-butanol. The individual fractions were investigated by thin layer chromatography to determine their content of the required compound. The fractions which contained the desired compound were combined and evaporated. 1.6 g of a yellowish foam were obtained, with a Rf value of 0.28 (TLC pre-coated plates, silica gel 60; running agent; chloroform/ethyl acetate/methanol/25% strength ammonia 80:80:80:2).

Rf=0.43 (running agent 1).

EXAMPLE 8

2-Acetylaminomethyl-2-hydroxymethyl-3,4,5-trihydroxypiperidine

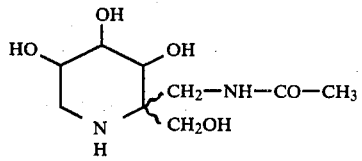

5.1 ml of acetic anhydride are added to a solution of 6.5 g of crude 2-aminomethyl-2-hydroxymethyl-3,4,5-trihydroxy-piperidine in 65 ml of methanol/water (1:1) at 0° C. The mixture is stirred at 0° C. for 30 minutes and at room temperature for 18 hours. The solution is concentrated in vacuo, the residue is dissolved in a little water and, to remove the acetic acid formed, the solution is filtered through an anion exchanger in the OH⊖ form and the column is washed with water. The filtrate is concentrated, the residue is dissolved in a little water and the solution is discharged onto a cellulose column 120 cm long and 3 cm wide which contains butanol as the mobile phase. The column is eluted with butanol, 95% pure butanol and 90% pure butanol and the individual fractions are investigated by thin layer chromatography to determine their content of the required compound. The fractions containing the desired product are collected and concentrated. The residue is dissolved in hot methanol and the solution is filtered and concentrated down to a volume of 30 ml. The product crystallises out. The crystallisation is brought to completion by leaving the mixture to stand overnight. The product is filtered off and washed with methanol. 2.7 g of colourless crystals of melting point 196° C. (decomposition) are obtained.

EXAMPLE 9

1-Methyl-2-benzoylaminomethyl-2-hydroxymethyl-3,4,5-trihydroxy-piperidine

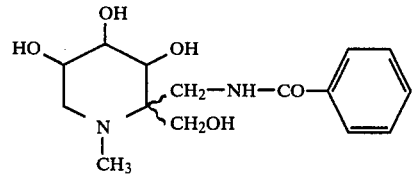

3.95 g of 2-benzoylaminomethyl-2-hydroxymethyl-3,4,5-trihydroxy-piperidine are dissolved in 40 ml of absolute methanol, and 3.24 ml of acetic acid and 7.8 ml of aqueous 35% strength formaldehyde solution are added successively. The mixture is cooled to 0° C. and 1.36 g of sodium cyanoborohydride are added. The mixture is allowed to warm slowly to room temperature and is stirred overnight. The solution is concentrated, the residue is dissolved in 40 ml of methanol/water (2:1) and the solution is discharged onto a column 40 cm long and 3 cm wide which contains a cation exchanger in the H+ form. The column is washed with about 1 l of methanol/water (2:1) and then with 0.5% strength ammonia in methanol/water (2:1).

The individual fractions are investigated by thin layer chromatography and the fractions containing the required product are collected and concentrated. The evaporation residue is dissolved in absolute methanol and, after adding a filtration auxiliary, the solution is filtered and concentrated. 2.8 g of a yellowish foam are obtained, with a Rf value of 0.2 (TLC pre-coated plates, silica gel 60; running agent: chloroform/ethyl acetate/methanol/25% strength ammonia 80:80:80:2).

Rf value=0.565 (running agent 1); 0.159 (running agent 2).

EXAMPLE 10

1-Ethyl-2-benzoylaminomethyl-2-hydroxymethyl-3,4,5-trihydroxy-piperidine was prepared analogously to Example 9, with a Rf value of 0.42 (TLC pre-coated plates, silica gel 60; running agent: chloroform/ethyl acetate/methanol/25% strength ammonia 80:80:80:2).

Rf=0.636 (running agent 1).

EXAMPLE 11

2-2-Amino-2-hydroxymethyl-3,4,5-trihydroxypiperidine dihydrochloride

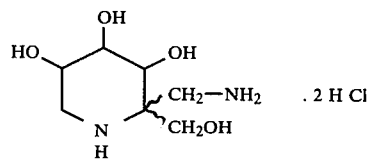

15 g of 2,6-imino-2-hydroxymethyl-2,6-didesoxy-L-ido(L-gulo)-hexonic acid nitrile (Example 1) are catalytically hydrogenated in 200 ml of water in the presence of Raney nickel under a pressure of 3.5 bars. The catalyst is filtered off, 80 ml of 1 N hydrochloric acid are added to the solution, and the mixture is concentrated. The resulting residue crystallises on concentrating with methanol. Methanol is added and the product is filtered off and washed with methanol. 12.4 g of 2-aminomethyl-2-hydroxymethyl-3,4,5-trihydroxypiperidine dihydrochloride of melting point 245° C., with decomposition, are obtained.

EXAMPLE 12

2-(N$^1$-Phenylureidomethyl)-2-hydroxymethyl-3,4,5-trihydroxypiperidine

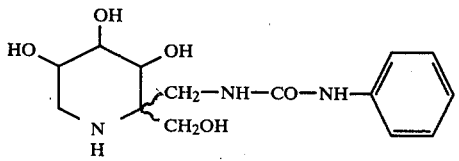

7.95 g (30 mmols) of 2-aminomethyl-2-hydroxymethyl-3,4,5-trihydroxy-piperidine dihydrochloride (Example 11) are dissolved in a mixture of 60 ml (60 mmols) of 1 N potassium hydroxide solution and 60 ml of methanol, and 4.9 ml (42 mmoles) of phenyl isocyanate are added dropwise at −10° C. The mixture is stirred at 20° C. for 5 hours, a further 2 ml of phenyl isocyanate are added and the mixture is stirred for 20 hours. It is diluted with 50 ml of water and extracted with 2× with ether. The aqueous phase is concentrated, the evaporation residue is taken up in a little methanol and the solution is discharged onto a column 120 cm long and 4 cm wide which contains cellulose as the stationary phase and acetone as the mobile phase. The column is eluted successively with acetone, 95% pure acetone and finally 90% pure acetone. The individual fractions are investigated by thin layer chromatography to determine their content of the required compound. The fractions containing the desired product are collected and evaporated. 5.8 g of 2-(N$^1$-phenylureidomethyl)-2-hydroxymethyl-3,4,5-trihydroxypiperidine are obtained as a colourless foam.

Rf value=0.294 (running agent 1)

Mass spectrum: the most important peaks in the upper mass range are: m/e=280; m/e=186; and m/e=162.

EXAMPLE 13

2-(N′-Allyl-thioureidomethyl)-2-hydroxymethyl-3,4,5-trihydroxypiperidine

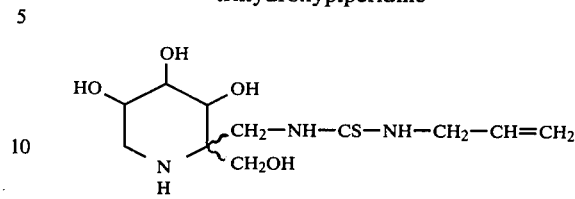

2.65 g (10 mmols) of 2-aminomethyl-2-hydroxymethyl-3,4,5-trihydroxypiperidine dihydrochloride (Example 11) are dissolved in a mixture of 20 ml of 1 N sodium hydroxide solution and 40 ml of methanol, and 2.0 ml of allyl isothiocyanate in 20 ml of ethyl acetate are added dropwise, whilst cooling with ice. The mixture is stirred at room temperature for 18 hours and concentrated. The evaporation residue is stirred with a little methanol; the insoluble salt is filtered off and the filtrate is discharged onto a column 120 cm long and 4 cm wide which contains cellulose as the stationary phase and acetone as the mobile phase. The column is eluted with acetone and then with aqueous acetone solution, the water content of which is increased. The individual fractions are examined by thin layer chromatography. The fractions containing the desired product are collected and concentrated. 1.5 g of 2-(N-allyl-thioureidomethyl)-2-hydroxymethyl-3,4,5-trihydroxypiperidine are obtained as an almost colourless amorphous solid product.

Mass spectrum: the most important peaks in the upper mass region are: m/e=260; m/e=234; m/e=203; and m/e=162. Rf value=0.343 (running agent 1); and 0.483 (running agent 3)

EXAMPLE 14

N-Hydroxyethyl-2-benzoylaminomethyl-2-hydroxymethyl-3,4,5-trihydroxypiperidine

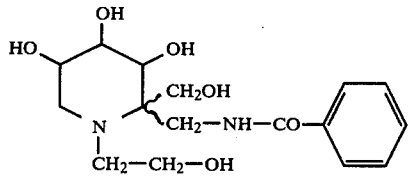

4.44 g of 2-benzoylaminomethyl-2-hydroxymethyl-3,4,5-trihydroxypiperidine (Preparation example 3) are dissolved in 65 ml of water and, after adding one drop of acetic acid, 6 ml of ethylene oxide are added at about 5° C. After stirring the mixture for 24 hours, the reaction has ended. The mixture is concentrated, the residue is dissolved in about 40 ml of methanol/water 2:1 and the solution is discharged onto a column 20 cm long and 3 cm wide which contains Amberlite ® IR 120, H+ form. The column is washed thoroughly with methanol/water 2:1 and then eluted with 0.1% strength ammonia. The individual fractions are investigated by thin layer chromatography to determine their content and the fractions containing the desired product are concentrated. 2.4 g of N-hydroxyethyl-2-benzoylaminomethyl-2-hydroxymethyl-3,4,5-trihydroxypiperidine are obtained in the form of a solid foam.

Mass spectrum: the most important peaks in the upper mass region are: m/e=309; m/e=291; m/e=206 and m/e=188. Rf value=0.50 (running agent 1).

EXAMPLE 15

N-Nonyl-2-benzoylaminomethyl-2-hydroxymethyl-3,4,5-trihydroxypiperidine

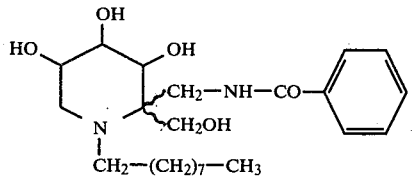

2.96 g of 2-benzoylaminomethyl-2-hydroxymethyl-3,4,5-trihydroxypiperidine (Example 3) are dissolved in a mixture of 40 ml of methanol, 2 ml of water and 2.7 ml of acetic acid, and 5.7 ml of nonylaldehyde are added. The solution is cooled to 5° C. in an ice-bath; 1.35 g of sodium cyanoborohydride are then added. The mixture is stirred for 30 minutes, whilst cooling, and then at room temperature for 24 hours. It is concentrated, the residue is dissolved in 30 ml of methanol/water 6:1 and the solution is discharged onto a column 30 cm long and 3 cm wide which is filled with Amberlite IR 120, H+ form. The column is washed thoroughly with methanol/water in the ratio 8:1 and then eluted with 0.2% strength ammonia in methanol/water 6:1. The pure fractions, determined by thin layer chromatography, are combined and concentrated. 2.6 g of an almost colourless oil are obtained.

Mass spectrum: the most important peaks in the upper mass region are: m/e=391; m/e=373; m/e=288; and m/e=228. Rf value=0.516 (running agent 2).

EXAMPLE 16

2-(2-Nitro-benzenesulphamidomethyl)-2-hydroxymethyl-3,4,5-trihydroxypiperidine

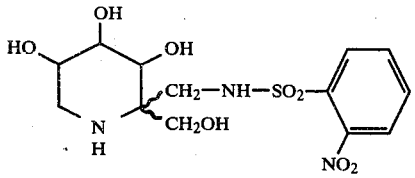

3.3 g of 2-aminomethyl-2-hydroxymethyl-3,4,5-trihydroxypiperidine dihydrochloride (Preparation example 11) are stirred with 14 g of potassium carbonate in 150 ml of dimethylformamide for 30 minutes. The mixture is cooled to 0° C. and 6.6 g of 2-nitrobenzenesulphonic acid chloride are added. The mixture is stirred for 24 hours and filtered and the residue is washed with dimethylformamide. The filtrate is concentrated, the evaporation residue is partitioned in water/ethyl acetate and the phases are separated. The aqueous phase is purified by the processes described above, over a column which contains Amberlite IR 120, H+ form. 2.6 g of 2-(2-nitrobenzenesulphamidomethyl)-2-hydroxymethyl-3,4,5-trihydroxypiperidine are obtained in the form of a yellowish foam.

Mass spectrum: the most important peaks in the upper mass region are: m/e=346; m/e=186; and m/e=162. Rf value=0.34 (running agent 1).

EXAMPLE 17

N-Methyl-2-dimethylaminomethyl-2-hydroxymethyl-3,4,5-trihydroxypiperidine

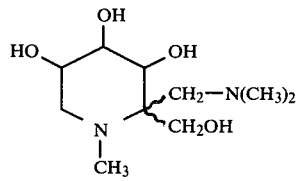

2.65 g of 2-aminomethyl-2-hydroxymethyl-3,4,5-trihydroxypiperidine dihydrochloride (Preparation example 11) are dissolved in a mixture of 30 ml of methanol, 16 ml of 35% strength formaldehyde solution and 3.6 ml of acetic acid, and 3.3 g of sodium cyanoborohydride are added at 0°–5° C. The mixture is stirred at room temperature for 20 hours and concentrated. The resulting evaporation residue is dissolved in methanol/water in the ratio of 6:1 and the solution is discharged onto a column 30 cm long and 3 cm wide which contains Amberlite IR 120, H+ form. The column is washed with about 2 l of methanol/water in the ratio 6:1 and is then eluted with 0.2% strength ammonia in methanol/water 6:1. The individual fractions are investigated by thin layer chromatography to determine their content. The fractions containing the desired product are combined and concentrated. The resulting product crystallises out of a little acetone. 1.4 g of colourless crystals of melting point 76° C. are obtained.

EXAMPLE 18

2-(Cyclododecylaminomethyl)-2-hydroxymethyl-3,4,5-trihydroxypiperidine

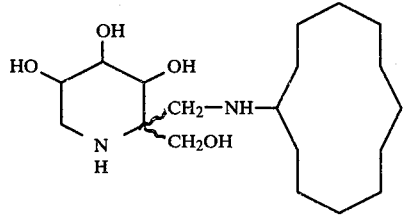

2.65 g of 2-aminomethyl-2-hydroxymethyl-3,4,5-trihydroxypiperidine dihydrochloride (Preparation example 11) are dissolved in 21 ml of water, and 60 ml of methanol 1.5 ml of acetic acid and 6 g of cyclododecanone are then added. When a solution is obtained, 1.35 g of sodium cyanoborohydride are added. The mixture is stirred for 18 hours and the product which has precipitated is filtered off and washed with water. 2.4 g of a colourless complex are obtained, and the complex is discharged onto an Amberlite IR 120 H+ exchange column to liberate the base. The column is washed with about 3 l of water and the desired compound is liberated with 2% strength aqueous ammonia. The product fractions, determined by thin layer chromatography, are collected and concentrated. The evaporation residue crystallises on trituration with isopropanol. 1.8 g of a colourless product of melting point 171°–172° C. are obtained.

EXAMPLE 19

2-Hexyloxycarbonylaminomethyl-2-hydroxymethyl-3,4,5-trihydroxypiperidine

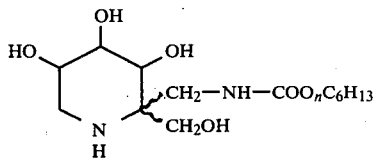

5.3 g of 2-aminomethyl-2-hydroxymethyl-3,4,5-trihydroxypiperidine dihydrochloride (Example 11) are dissolved in 20 ml of water, and 30 ml of methanol and 8.4 ml of triethylamine are added. 7.8 ml of chloroformic acid hexyl ester, dissolved in 30 ml of ethyl acetate are added dropwise to this solution at 0°–5° C. After stirring the mixture at room temperature for three hours, it is concentrated. The evaporation residue is partitioned in water/ethyl acetate, the phases are separated and the ethyl acetate phase is washed 1× with water. The combined aqueous phases are stirred with 80 g of Amberlite IR A 400, OH⁻ form for 1 hour, the mixture is filtered and the filtrate is concentrated. The evaporation residue is dissolved in a little methanol and the solution is discharged onto a column 120 cm long and 4 cm wide which contains cellulose as the stationary phase and acetone as the mobile phase. The column is washed with acetone. The substance is obtained by elution with 95% pure acetone. After concentrating the eluate, 2.4 g of an almost colourless yellow foam are obtained.

RF value: 0.542 (running agent 1); and 0.143 (running agent 2).

Further preparation examples are given in the tables below.

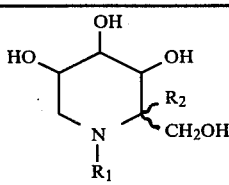

| Example No. | $R_1$ | $R_2$ | Analogously to Example No. | Important mass peaks m/e | Rf value (running agent) |
|---|---|---|---|---|---|
| 20 | H | $-CH_2-NH-CO-C_6H_{13}$ | 3 | 273, 162 | 0,453 (1) |
| 21 | $-nC_{11}H_{23}$ | $-CH_2-NH-CO-\langle\text{Ph}\rangle$ | 15 | 419, 316, 286 | 0,524 (2) |
| 22 | $-nC_4H_9$ | $-CH_2-NH-CO-\langle\text{Ph}\rangle$ | 15 | 321, 218 | 0,421 (2) |
| 23 | $CH_3$ | $-CH_2-NH-CO-nC_6H_{13}$ | 9 | 287, 269, 176 | 0,607 (1) |
| 24 | $-nC_9H_{19}$ | $-CH_2-NH-CO-nC_6H_{13}$ | 15 | 399, 288 | 0,879 (1) |
| 25 | $n\text{-}C_7H_{15}$ | $-CH_2-NH-CO-\langle\text{Ph}\rangle$ | 15 | 363, 260, 230 | 0,484 (2), |
| 26 | $-C_3H_7$ | $-CH_2-NH-CO-\langle\text{Ph}\rangle$ | 15 | 307, 204 | 0,389 (2), |
| 27 | H | $-CH_2-NH-CO-C_8H_{17}$ | 3 | 314, 301, 162 | 0,495 (1) |
| 28 | H | $-CH_2-NH-CH(CH_3)-(CH_2)_3-N(C_2H_5)_2$ | 18 | 333, 258, 243, 162 | 0,415 |
| 29 | H | $-CH_2-NH-SO_2-\langle\text{Ph}\rangle-NO_2$ | 16 | 346, 202, 162 | 0,34 (1) |
| 30 | H | $-CH_2-NH-CO-NH-\langle\text{Ph}\rangle-Cl$ | 12 | 235, 187, 162 | 0,302 (1), 0,402 (3) |
| 31 | H | $-CH_2-NH-CO-NH-CH_3$ | 12 | 218, 187, 162 | 0,146 (1), 0,119 (3) |
| 32 | H | $-CH_2-NH-CO-NH-C_2H_5$ | 12 | 232, 187, 162 | 0,198 (1), 0,184 (3) |
| 33 | H | $-CH_2-NH-CO-NH-\langle\text{Ph}\rangle-OC_2H_5$ | 12 | 187, 163, 163 | 0,292 (1), 0,352 (3) |
| 34 | H | $-CH_2-NH-CO-NH-\langle\text{Ph}\rangle-CH=CH-COOC_2H_5$ | 12 | 217, 191, 187, 162 | 0,368 (1), 0,419 (3) |

-continued

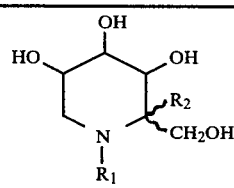

| Example No. | $R_1$ | $R_2$ | Analogously to Example No. | Important mass peaks m/e | Rf value (running agent) |
|---|---|---|---|---|---|
| 35 | H | —CH$_2$—NH—CO—NH—CH$_2$—C$_6$H$_5$ | 12 | 187<br>162<br>106 | 0,307 (1)<br>0,328 (3) |
| 36 | H | —CH$_2$—NH—CO—NH—C$_6$H$_4$—CH$_3$ | 12 | 187<br>162<br>133 | 0,311 (1)<br>0,377 (3) |
| 37 | H | —CH$_2$—NH—CO—NH—C$_6$H$_4$(CF$_3$) | 12 | 187<br>162<br>161 | 0,321 (1) |
| 38 | H | —CH$_2$—NH—CO—NH—C$_{12}$H$_{25}$ | 13 | 187<br>169<br>162 | |
| 39 | H | —CH$_2$—NH—CS—NH—C$_6$H$_5$ | 12 | 234<br>203<br>162<br>93 | 0,454 (1) |
| 40 | H | —CH$_2$—NH—CS—NH—CH$_3$ | 12 | 234<br>203<br>162 | 0,222 (1)<br>0,308 (3) |
| 41 | H | —CH$_2$—NH—CO—NH—C$_6$H$_{11}$ | 12 | 286<br>187<br>162<br>99 | 0,352 (1) |
| 42 | H | —CH$_2$—NH—CO—NH—C$_6$H$_4$—NO$_2$ | 13 | Schmp.:<br>206° C. | |
| 43 | H | —CH$_2$—NH—CO—NH—CH$_2$—CH=CH$_2$ | 13 | 244<br>187<br>162 | 0,241 (1)<br>0,217 (3) |
| 44 | CH$_3$ | —CH$_2$—NH—CO—NH—C$_6$H$_5$ | 9 | 201<br>176<br>119 | 0,426 (1) |
| 45 | H | —CH$_2$—NH—CO—NH—C$_4$H$_9$ | 13 | | 0,275 (3) |
| 46 | H | —CH$_2$—NH—CO—NH—C$_6$H$_4$—CH$_3$ | 13 | 187<br>162<br>133 | 0,315 (1) |
| 47 | CH$_3$ | —CH$_2$—NH—CS—NH—C$_6$H$_5$ | 9 | | 0,692 (3) |
| 48 | H | —CH$_2$—NH—CO—NH—C$_6$H$_4$—F | 13 | 311<br>280<br>187<br>162 | 0,287 (1)<br>0,392 (1) |
| 49 | H | —CH$_2$—NH—CO—CH$_2$—OCH$_3$ | 13 | | 0,148 (1) |
| 50 | H | —CH$_2$—NH—CO—NH—P(O)(OC$_2$H$_5$)(C$_2$H$_5$) | 13 | | 0,271 (1) |
| 51 | —C$_6$H$_{13}$ | —CH$_2$—N(C$_6$H$_{13}$)$_2$ | 17 | | 0,825 (2) |
| 52 | H | —CH$_2$—NH—CO—NH—(CH$_2$)$_5$—CN | 13 | | 0,308 (1) |
| 53 | H | —CH$_2$—NH—CO—NH$_2$ | 13 with cyanic acid | | 0,0695 (1) |
| 54 | H | —CH$_2$—NH—CO—NH—(CH$_2$)$_2$—COOiC$_4$H$_9$ | 13 | | 0,417 (1) |
| 55 | H | —CH$_2$—NH—COOCH$_3$ | 19 | | 0,278 (1) |

Among the new 3,4,5-trihydroxypiperidine derivative salts of the invention, those salts that are pharmaceutically acceptable (and especially such acid addition salts) are particularly important and are preferred.

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation.

Therapeutically useful acids are, for example, inorganic acids, e.g., hydrochloric, hydrobromic, sulfuric, phosphoric, nitric or perchloric acid, or organic acids., e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

New free 3,4,5-trihydroxypiperidine derivatives of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A 3,4,5-trihydroxypiperidine derivative of the formula

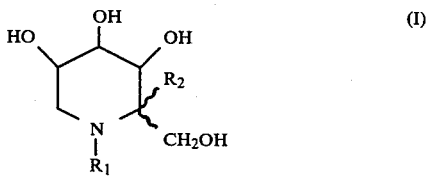

(I)

or a pharmaceutically acceptable salt thereof, in which
$R_1$ denotes a hydrogen atom, an amino group, an alkyl radical with 1 to 30 carbon atoms, an alkenyl or alkinyl radical with 2 to 18 carbon atoms, said alkyl, alkenyl or alkinyl radicals substituted by hydroxy, $C_1$-$C_4$-alkoxy, $C_1$-$C_7$-alkanoyloxy, phenylcarbonyloxy, trifluoromethyl, amino, $C_1$-$C_4$-alkylamino, $C_1$-$C_4$-dialkylamino, mercapto, $C_1$-$C_4$-alkylmercapto, halogen, $C_1$-$C_4$-alkylcarbonyl, carboxyl, nitro or cyano, phenyl or naphthyl; cycloalkyl, cycloalkenyl or cycloalkadienyl having 3 to 10 carbon atoms; or mono- or bi-cyclic carbocyclic aryl having 6 or 10 carbon atoms and
$R_2$ denotes a —$CH_2NR_3R_4$, —$CH_2$—$NR_3$—CO—$R_4$, —$CH_2$—$NR_3$—$CONR_4R_5$, —$CH_2$—$NR_3$—$SO_2R_4$, —$CH_2$—$NR_3$—$SO_2$—$NR_4R_5$, —$CH_2$—$NR_3$—CS—$R_4$, —$CH_2$—$NR_3$—CS—$NR_4R_5$, —COOH, —$CONH_2$, —$COOR_3$, —CO—$NR_3R_4$, —$CH_2$—$OR_3$, —$CH_2$—NH—$COOR_4$ or —$CH_2$—NH—$COSR_4$ group in which
$R_3$ denotes hydrogen or, independently of $R_4$, one of the meanings given for $R_4$, and
$R_4$ and $R_5$ independently denote hydrogen; $C_1$-$C_{30}$-alkyl; $C_2$-$C_{18}$-alkenyl; $C_3$-$C_{10}$-cycloalkyl; $C_3$-$C_{10}$-cycloalkenyl; $C_3$—$C_{10}$-cycloalkadienyl; $C_1$-$C_{30}$-alkyl or $C_2$-$C_{18}$-alkenyl substituted by hydroxy, $C_1$-$C_4$-alkoxy, $C_1$-$C_4$-carbalkoxy, carboxy or cyano; a mono- or bi-cyclic carbocyclic aryl radical with 6 or 10 carbon atoms; phenyl substituted by $C_1$-$C_4$-alkyl, $C_1$-$C_4$-alkoxy, halogen, nitro, trifluoromethyl or —CH=$CH_2COOC_2H_5$; or benzyl which is unsubstituted or substituted by methyl, methoxy, chlorine or nitro.

2. A compound according to claim 1, in which $R_1$, $R_3$, $R_4$ and $R_5$ independently of one another denote a hydrogen atom, an alkyl radical with 1 to 30 carbon atoms, an alkenyl radical or alkinyl radical with 2 to 18 carbon atoms, cycloalkyl, cycloalkenyl or cycloalkadienyl with 3 to 10 carbon atoms, or a mono- or bi-cyclic carbocyclic aryl radical with 6 or 10 carbon atoms.

3. A compound according to claim 2, in which $R_1$, $R_3$, $R_4$ and $R_5$ independently of one another denote a hydrogen atom an alkyl radical with 1 to 18 carbon atoms, an alkenyl radical or alkinyl radical with 3 to 10 carbon atoms, cycloalkyl, cycloalkenyl or cycloalkadienyl with 3 to 10 carbon atoms, or a mono- or bi-cyclic carbocyclic aryl radical with 6 to 10 carbon atoms:

4. A compound according to claim 1, of the formula

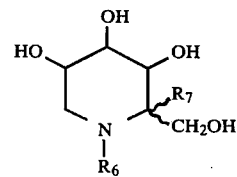

(II)

or a pharmaceutically acceptable salt thereof, in which
$R_6$ denotes a hydrogen atom or a $C_1$ to $C_{12}$ alkyl or phenyl-$C_1$ to $C_4$ alkyl group.
$R_7$ denotes —$CH_2$—$NHR_8$, —$CH_2$—$NHCOR_9$, —$CH_2$—NH—$SO_2NR_8R_9$, —$CH_2$—NH—$CONHR_8$, —$CH_2$—NH—$SO_2R_9$, —$CH_2$—NH—$CSNHR_8$, —$CONH_2$, —CO—$NR_8R_9$, —$COOR_8$ or —$CH_2OH$,
$R_8$ denotes a hydrogen atom or, independently of $R_9$, has any of those meanings given for $R_9$, and
$R_9$ denotes a $C_1$ to $C_{20}$ alkyl, allyl or $C_5$ or $C_6$ cycloalkyl radical, a phenyl radical which is optionally substituted by methyl, methoxy, chlorine or nitro, a benzyl radical which is optionally substituted by methyl, methoxy, chlorine or a nitro radical.

5. A compound according to claim 4, in which $R_7$ has the same meaning as in claim 4 except that, in the case of radicals —$CH_2$—NH—$CONHR_8$ and —$CH_2$—NH—$CSNHR_8$, $R_8$ only denotes independently of $R_9$, any of those radicals given for $R_9$.

6. A compound according to claim 1 of the formula

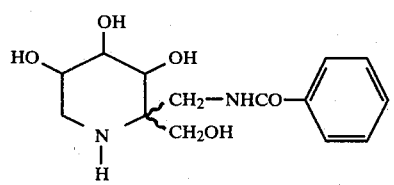

7. A compound according to claim 1 of the formula

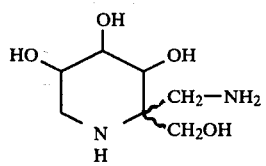

8. A compound according to claim 1 of the formula

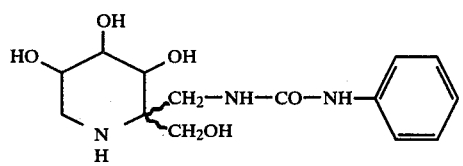

9. A compound according to claim 1 of the formula

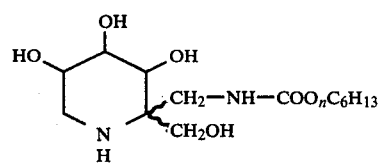

10. A compound according to claim 1 of the formula

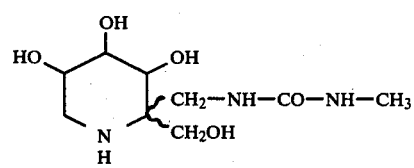

11. A compound according to claim 1 of the formula

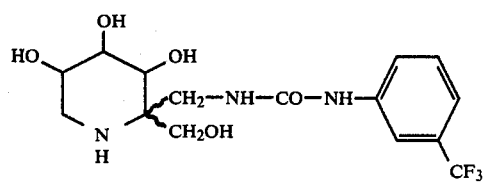

12. A compound according to claim 1 of the formula

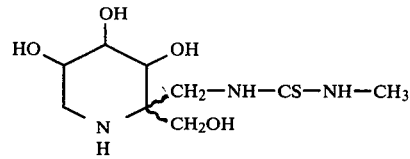

13. A compound according to claim 1 of the formula

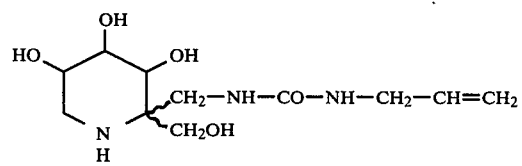

14. A compound according to claim 1 of the formula

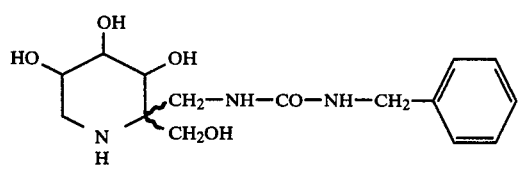

15. A compound according to claim 1 of the formula

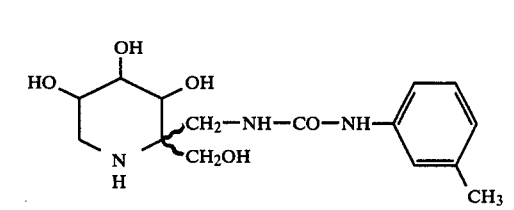

16. A compound according to claim 1 of the formula

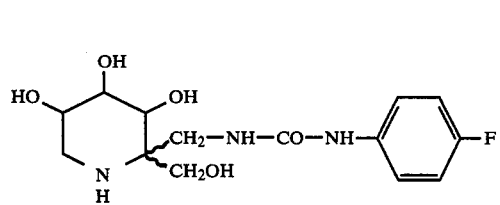

17. A compound according to claim 1 of the formula

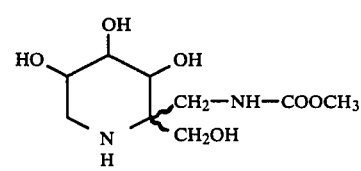

18. A pharmaceutical composition containing as an active ingredient an amount effective for combatting diabetes, hyperlipaemia, adiposity or arteriosclerosis of a compound according to claim 1 in admixture with a pharmaceutically acceptable solid, liquid or liquefied gaseous diluent.

19. A pharmaceutical composition of claim 18 in the form of a sterile or physiologically isotonic aqueous solution.

20. A composition according to claim 18 containing from 0.1 to 99.5% by weight of the said active ingredient.

21. A medicament in dosage unit form comprising an amount effective for combating diabetes, hyperlipaemia, adiposity or arteriosclerosis of a compound according to claim 1 together with an inert pharmaceutical carrier.

22. A medicament of claim 21 in the form of tablets, pills, dragees, capsules, ampoules or suppositories.

23. A method of combating arteriosclerosis, adiosity, diabetes and/or hyperlipaemia in warm-blooded animals which comprises administering to the animals an effective amount of an active compound according to claim 1 either alone or in admixture with a pharmaceutically acceptable diluent or in the form of a medicament.

24. A method according to claim 23 in which the active compound is administered in an amount of 0.1 to 100 mg per kg body weight per day.

25. A method according to claim 24 in which the active compound is administered orally.

26. A medicated fodder comprising an amount effective for influencing the lean meat/fat ratio in favor of the proportion of lean meat of an active compound as claimed in claim 1 and a nutritious material.

27. A medicated fodder according to claim 26 containing 0.02 to 20% by weight of the active compound.

* * * * *